United States Patent
Castner et al.

(10) Patent No.: US 9,687,571 B2
(45) Date of Patent: Jun. 27, 2017

(54) STABILIZATION OF RADIOPHARMACEUTICAL COMPOSITIONS USING ASCORBIC ACID

(75) Inventors: James F. Castner, Groton, MA (US); Dianne D. Zdankiewicz, Londonderry, NH (US); James E. Anderson, Hudson, MA (US)

(73) Assignee: Lantheus Medical Imaging, Inc., North Billerica, MA (US)

( * ) Notice: Subject to any disclaimer, the term of this patent is extended or adjusted under 35 U.S.C. 154(b) by 931 days.

(21) Appl. No.: 13/264,276

(22) PCT Filed: Apr. 15, 2010

(86) PCT No.: PCT/US2010/001120
§ 371 (c)(1),
(2), (4) Date: Jun. 7, 2012

(87) PCT Pub. No.: WO2010/120368
PCT Pub. Date: Oct. 21, 2010

(65) Prior Publication Data
US 2012/0237445 A1 Sep. 20, 2012
US 2013/0101508 A9 Apr. 25, 2013

Related U.S. Application Data

(60) Provisional application No. 61/169,353, filed on Apr. 15, 2009.

(51) Int. Cl.
A61K 51/00 (2006.01)
A61M 36/14 (2006.01)
A61K 51/04 (2006.01)

(52) U.S. Cl.
CPC .......... *A61K 51/04* (2013.01); *A61K 51/0421* (2013.01); *A61K 51/0453* (2013.01); *A61K 51/0455* (2013.01); *A61K 51/0459* (2013.01)

(58) Field of Classification Search
CPC .... A61K 51/00; A61K 51/04; A61K 51/0421; A61K 51/0453; A61K 51/0455; A61K 51/0459
USPC .... 424/1.11, 1.65, 1.81, 1.85, 1.89, 9.1, 9.2, 424/9.3, 9.4, 9.5, 9.6; 514/1, 785
See application file for complete search history.

(56) References Cited

U.S. PATENT DOCUMENTS

| | | | |
|---|---|---|---|
| 3,359,103 A | 12/1967 | Becker et al. | |
| 4,510,125 A * | 4/1985 | Grogg et al. | 424/1.77 |
| 5,011,676 A | 4/1991 | Thakur | |
| 5,087,440 A | 2/1992 | Cacheris et al. | |
| 5,088,499 A | 2/1992 | Unger | |
| 5,093,105 A | 3/1992 | Flanagan et al. | |
| 5,155,215 A | 10/1992 | Ranney | |
| 5,169,848 A | 12/1992 | Bettarini et al. | |
| 5,169,942 A | 12/1992 | Johnson | |
| 5,228,446 A | 7/1993 | Unger et al. | |
| 5,281,704 A | 1/1994 | Love et al. | |
| 5,306,482 A | 4/1994 | Tartaglia et al. | |
| 5,377,681 A | 1/1995 | Drane | |
| 5,384,113 A | 1/1995 | Deutsch et al. | |
| 5,393,512 A | 2/1995 | Vanderheyden et al. | |
| 5,412,148 A | 5/1995 | Keana | |
| 5,417,959 A | 5/1995 | Wallace | |
| 5,436,325 A | 7/1995 | Johnson et al. | |
| 5,520,904 A | 5/1996 | Nosco et al. | |
| 5,547,656 A | 8/1996 | Unger | |
| 5,567,411 A | 10/1996 | Keana et al. | |
| 5,585,112 A | 12/1996 | Unger et al. | |
| 5,587,491 A | 12/1996 | Hoye et al. | |
| 5,679,810 A | 10/1997 | Love et al. | |
| 5,760,191 A | 6/1998 | Snow et al. | |
| 5,801,228 A | 9/1998 | Hollister et al. | |
| 5,804,161 A | 9/1998 | Long et al. | |
| 5,846,517 A | 12/1998 | Unger | |
| 5,961,955 A | 10/1999 | Shochat et al. | |
| 6,056,939 A | 5/2000 | Desreux et al. | |
| 6,066,309 A | 5/2000 | Zamora et al. | |
| 6,241,964 B1 | 6/2001 | Burns et al. | |
| 6,565,889 B2 | 5/2003 | Zasadzinski et al. | |
| 6,713,042 B2 | 3/2004 | Liu | |
| 7,060,251 B1 * | 6/2006 | Elmaleh et al. | 424/9.4 |
| 7,112,318 B2 | 9/2006 | Madar et al. | |
| 7,344,702 B2 * | 3/2008 | Casebier et al. | 424/1.89 |
| 7,410,998 B2 | 8/2008 | Nicolaou et al. | |
| 7,485,283 B2 | 2/2009 | Radeke et al. | |
| 7,824,659 B2 | 11/2010 | Casebier et al. | |

(Continued)

FOREIGN PATENT DOCUMENTS

CN 101555232 A 10/2009
EP 0169375 A2 1/1986
(Continued)

OTHER PUBLICATIONS

Scott et al, Applied Radiation and Isotopes, vol. 67, No. 1, Jan. 2009, pp. 88-94.*
International Search Report and Written Opinion for PCT/US2011/057358 mailed May 9, 2012.
International Preliminary Report on Patentability forPCT/US2011/057358 mailed May 1, 2014.
Ballinger et al., Stabilization of 99mTc-pyrophosphate injection with gentisic acid. Eur J Nucl Med. Apr. 1981;6(4):153-4.
Liu et al., Ascorbic acid: useful as a buffer agent and radiolytic stabilizer for metalloradiopharmaceuticals. Bioconjug Chem. Sep.-Oct. 2003;14(5):1052-6.
Subramanian et al, eds, Radiopharmaceuticals. Society of Nuclear Medicine, New York, 1975:37-38.
Tofe et al., in vitro stabilization of a low-tin bone-imaging agent (99mTc-Sn-HEDP) by ascorbic acid. J Nucl Med. Sep. 1976;17(9):820-5.

(Continued)

*Primary Examiner* — D L Jones
(74) *Attorney, Agent, or Firm* — Wolf, Greenfield & Sacks, P.C.

(57) ABSTRACT

Radiopharmaceutical compositions, and related methods, useful for medical imaging are provided. The radiopharmaceutical compositions include one or more radiopharmaceutical compounds, together with a stabilizer comprising ascorbic acid, wherein the pH of said composition is within the range of about 3.5-5.5.

12 Claims, 3 Drawing Sheets

(56) References Cited

U.S. PATENT DOCUMENTS

| | | | |
|---|---|---|---|
| 7,847,092 B2 | 12/2010 | Moon et al. | |
| 8,226,929 B2 | 7/2012 | Casebier et al. | |
| 8,263,042 B2 | 9/2012 | Radeke et al. | |
| 8,936,777 B2 | 1/2015 | Cesati et al. | |
| 9,115,172 B2 * | 8/2015 | D'Souza et al. | |
| 9,161,997 B2 * | 10/2015 | Casebier | A61K 49/0002 |
| 9,408,927 B2 * | 8/2016 | Robinson | A61K 51/0459 |
| 2002/0122769 A1 | 9/2002 | Liu | |
| 2003/0044354 A1 | 3/2003 | Carpenter et al. | |
| 2003/0124054 A1 | 7/2003 | Toyohara et al. | |
| 2004/0033197 A1 | 2/2004 | Madar et al. | |
| 2004/0034239 A1 | 2/2004 | Nicolaou et al. | |
| 2004/0142972 A1 | 7/2004 | Edgar et al. | |
| 2005/0191238 A1 | 9/2005 | Casebier et al. | |
| 2005/0244332 A1 | 11/2005 | Radeke et al. | |
| 2006/0083681 A1 | 4/2006 | Purohit et al. | |
| 2007/0036716 A1 | 2/2007 | Casebier et al. | |
| 2007/0082879 A1 | 4/2007 | Goodman | |
| 2008/0112884 A1 | 5/2008 | Casebier et al. | |
| 2009/0104118 A1 | 4/2009 | Radeke et al. | |
| 2009/0297442 A1 | 12/2009 | Hemstad | |
| 2010/0236958 A1 | 9/2010 | Veggeland et al. | |
| 2011/0091374 A1 | 4/2011 | Robinson et al. | |
| 2014/0328757 A1 | 11/2014 | Castner et al. | |

FOREIGN PATENT DOCUMENTS

| | | |
|---|---|---|
| EP | 0 111 415 B1 | 4/1990 |
| EP | 0727225 A2 | 8/1996 |
| EP | 1 356 827 A1 | 10/2003 |
| JP | 63-15974 A | 7/1988 |
| JP | 2004-529884 A | 9/2004 |
| JP | 2006-528644 A | 12/2006 |
| JP | 2007-526916 A | 9/2007 |
| JP | 2009-500441 A | 1/2009 |
| WO | WO 91/14460 A1 | 10/1991 |
| WO | WO 92/17215 A1 | 10/1992 |
| WO | WO 94/22496 A1 | 10/1994 |
| WO | WO 95/33757 A1 | 12/1995 |
| WO | WO 00/78283 A1 | 12/2000 |
| WO | WO 02/20008 A1 | 3/2002 |
| WO | WO 02/067859 A2 | 9/2002 |
| WO | WO 03/002157 A1 | 1/2003 |
| WO | WO 03/065882 A2 | 8/2003 |
| WO | WO 03/082350 A2 | 10/2003 |
| WO | WO 03/086476 A1 | 10/2003 |
| WO | WO 2004/056400 A1 | 7/2004 |
| WO | WO 2005/009393 A2 | 2/2005 |
| WO | WO 2005/012319 A1 | 2/2005 |
| WO | WO 2005/079391 A2 | 9/2005 |
| WO | WO 2005/105159 A2 | 11/2005 |
| WO | WO 2007/007021 A1 | 1/2007 |
| WO | WO 2007/021858 A2 | 2/2007 |
| WO | WO 2008/099800 A1 | 8/2008 |
| WO | WO 2009/108376 A2 | 9/2009 |
| WO | WO 2009/110984 A2 | 9/2009 |
| WO | WO 2010/120368 A2 | 10/2010 |
| WO | WO 2011/097649 A2 | 8/2011 |
| WO | WO 2011/143360 A2 | 11/2011 |
| WO | WO 2013/036869 A2 | 3/2013 |

OTHER PUBLICATIONS

Bateman et al., Diagnostic accuracy of rest/stress ECG-gated Rb-82 myocardial perfusion PET: comparison with ECG-gated Tc-99m sestamibi SPECT. J Nucl Cardiol. Jan.-Feb. 2006;13(1):24-33.
Bergmann et al., Noninvasive quantitation of myocardial blood flow in human subjects with oxygen-15-labeled water and positron emission tomography. J Am Coll Cardiol. Sep. 1989;14(3):639-52.
Berman D.S., Germano.G, Slomka, P.J., (2012). Improvement in PET myocardial perfusion image quality and quantification with Flurpiridaz F 18. Journal of Nuclear Cardiology 19(1): S38-45.
Berman et al., (2010) Comparison of 18F-BMS747158 and 82Rb PET vs SPECT for detection of myocardial ischemia. Journal of Nuclear Cardiology 17(4): 743. Abstract #31.17.
Bousquet et al., Gd-DOTA: Characterization of a New Paramagnetic Complex. Radiology. 1988; 166(3): 693-8.
Brown et al., Delineation of myocardial oxygen utilization with carbon -11-labeled acetate. Circulatio. 1987; 76(3):687-96.
Cao et al., Synthesis and antifeedant activity of new oxadiazolyl 3(2H)-pyridazinones. J Agric Food Chem. Jan. 1, 2003;51(1):152-5.
Case J.A, Lazewatsky. J., Hsu B-L., Maddahi J., Berman D., Bateman T, (2010). Automatic registration of F-18 labeled BMS-747158 stress and rest myocardial perfusion images using 6D cross-correlation optimization. Journal of Nuclear Medicine 51(Supplement 2): 1687.
Case J.A, Lazewatsky. J., Hsu, BL, Maddahi J, Berman DS, Bateman TM, (2010). Iterative technique for optimizing injected tracer dosage and acquisition time for F-18 labeled myocardial perfusion tracer Flurpiridaz F-18. Journal of Nuclear Cardiology 17(4): 726. Abstract # 9.17.
Case JA, Lazewatsky JL, Cullom SJ, Berman DS, Maddahi J, Bateman TM, (2011). Impact of image filtering, BMI, and gender on optimal dosage acquisition time product using a novel PET myocardial perfusion tracer: F-18 labeled Flurpiridaz. Journal of Nuclear Cardiology 18(4): 769-770. Asbtract #14.32.
Case JA., TM Bateman, M Luangamath, JL Lazewatsky, DS Berman, J Maddahi., (2010). Independence of myocardial functional parameters (LVEF, EDV, and ESV) across a large range of acquisition times and measured from a novel F-18 radiotracer, Flurpiridaz F-18. Journal of Nuclear Cardiology 17(4 Supplement 1): 725-726. Abstract #9.15.
Case, JA; Maddahi, J; Bengel, FM; Bateman, T; Dahlbom, M; Lazewatsky, J., (2009) Imaging properties of F-18 labeled myocardial perfusion PET agent, BMS747158: dosage, acquisition time and scanner type. Journal of Nuclear Medicine 50 (Supplement 2): 418. 2 pages.
Chary et al., Reductive cleavage of acetals/ketals. Synthetic Communications. 1999;29(8):1257-1261.
Clark et al., The present role of nuclear cardiology in clinical practice. Q J Nucl Med Mol Imaging. Mar. 2005;49(1):43-58.
Clark, Fluoride ion as a base in organic synthesis. Chem. Rev. 1980; 80(5):429-52.
Crane P., Hayes, M. Cesati R, Spencer K., Sanga M, Robinson S, Onthank D., (2011) Use of a tritiated ($^3$H) analog of flurpiridaz F18 to characterize the pharmacokinetics, metabolism and excretion in normal human subjects. AAAPS. (2011) Abstract.
Di Carli et al., Cardiac PET-CT. J Thorac Imaging. Feb. 2007;22(1):101-6.
Di Carli et al., Clinical myocardial perfusion PET/CT. J Nucl Med. May 2007;48(5):783-93.
Esposti, M. D., Inhibitors of NADH—ubiquinone reductase: an overview. Biochimica et Biophysica Acta. 1998;1364: 222-35.
Garcia et al., What should we expect from cardiac PET? J Nucl Med. Jun. 1993;34(6):978-80.
Garrison et al., Reaction mechanisms in the radiolysis of peptides, polypeptides, and proteins. Chem Rev. 1987;87:381-98.
Ghesani et al., Role of F-18 FDG positron emission tomography (PET) in the assessment of myocardial viability. Echocardiography. Feb. 2005;22(2):165-77.
Glover et al., Journey to find the ideal PET flow tracer for clinical use: are we there yet? J Nucl Cardiol. Nov.-Dec. 2007;14(6):765-8.
Glover et al., Comparison between 201Tl and 99mTc sestamibi uptake during adenosine-induced vasodilation as a function of coronary stenosis severity. Circulation. Feb. 1, 1995;91(3):813-20.
Glover et al., Myocardial 99mTc-tetrofosmin uptake during adenosine-induced vasodilatation with either a critical or mild coronary stenosis: comparison with 201Tl and regional myocardial blood flow. Circulation. Oct. 7, 1997;96(7):2332-8.
Glover et al., Myocardial kinetics of Tc-MIBI in canine myocardium after dipyridamole. Circulation. Feb. 1990;81(2):628-37.
Gout et al., Sulfasalazine, a potent suppressor of lymphoma growth by inhibition of the $x_c$ cystine transporter: a new action for an old drug. Leukemia. 2001;15:1633-40.
Han et al., Total Synthesis of 34-hydroxyasimicin and Its Photoactive Derivative for Affinity Labeling of the Mitochondrial Complex I. Chemistry—A European Journal. 2004;10( 9):2149-58.

(56) References Cited

OTHER PUBLICATIONS

Higgins et al [3H]dihydrorotenone binding to NADH: ubiquinone reductase (complex I) of the electron transport chain: an autoradiographic study. J Neurosci. Jun. 15, 1996;16(12):3807-16.
Higuchi et al., A new 18F-labeled myocardial PET tracer: myocardial uptake after permanent and transient coronary occlusion in rats. J Nucl Med. Oct. 2008;49(10):1715-22. Epub Sep. 15, 2008.
Higuchi T; Huisman M.C., Nekolla S.G.; Wester H.J.; Poethko T; Schwaiger M; Casebier D.C., A Novel [F-18] labeled PET Tracer for the Characterization of Coronary Artery Disease: Preliminary Evaluation in a Coronary Occlusion Rat Model Circulation. 2007;116:II_658 Abstract #2947.
Hsu B, Logan J, Quirke A, Orlando L, Devine M, Dann R, Taillefer R, Lazewatsky J., (2011) Remote camera qualification (RCQ) of PET and PET/CT scanners for BMS747158 F18 myocardial perfusion phase 3 clinical trial using a standardized phantom procedure. J Nucl Med. 52 (Supplement 1):54.
Hsu B., Lazewatsky. J., Bateman T., Devine M., Maddahi J., Berman D. et al., (2010). Cardiac phantom simulation of dose injection parameters for one-day rest/stress myocardial perfusion tracer. Journal of Nuclear Medicine 51(Supplement 2): 320.
Huang et al., Rabbit myocardial 82Rb kinetics and a compartmental model for blood flow estimation. Am J Physiol. Apr. 1989;256(4 Pt 2):H1156-64.
Huang S, Dahlbom M, Truong D, Lazewatsky JC, Washburn D, Schelbert H, Czernin J, Phelps M, Maddahi J., (2011). Evaluation of absolute mbf at rest and stress with Flurpiridaz F-18 injection PET in normal subjects and patients with coronary artery disease (CAD) and in two types of scanners. Journal of Nuclear Cardiology 18(4): 783-784. Abstract #26.19.
Huang S-C, Dahlbom M, Maddahi J, Truong D, Lazewatsky J, Washburn D, Schelbert H, Czernin J, Phelps M., (2011) Streamlined quantification of absolute MBF at rest and stress with flurpiridaz F-18 injection PET in normal subjects and patients with coronary artery disease (CAD). J Nucl Med. 52 (Supplement 1):1114.
Huisman et al., Initial characterization of an 18F-labeled myocardial perfusion tracer. J Nucl Med. Apr. 2008;49(4):630-6. Epub Mar. 14, 2008.
Huisman M.; Higuchi T; Reder S; Nekolla S; Poethko T; Casebier D; Schwaiger M, First Preclinical Study of a New F-18 Labeled PET Tracer for Myocardial Perfusion Imaging Circulation. 2007;116:II_718 Abstract # 3193.
Igarashi et al., Summary of toxicology studies with Pyridaben. J Peticide Sci. 1994;19:Technical Information.
Jiang et al., Mimicry of annonaceous acetogenins: Enantioselective syntheiss of a (4R)-hydroxy analogue having potent antitumor activity. J. Org. Chem. 2002;67(10):3404-8.
Kagan, M. Bozek J., Spencer, K., Hsu B., Mistry M., Onthank D., Robinson S., Yu M., Comparison of flurpiridaz F 18 and FDG for assessment of left ventricular tissue mass following myocardial infarction in rats. Journal of Nuclear Medicine;2011:52( Supp. 1):1097.
Kann et al., Mitochondria and neuronal activity. Am J Physiol Cell Physiol. Feb. 2007;292(2):C641-57. Epub Nov. 8, 2006.
Knapp et al., Availability of rhenium-188 from the alumina-based tungsten-188/rhenium-188 generator for preparation of rhenium-188-labeled radiopharmaceuticals for cancer treatment. Anticancer Res. May-Jun. 1997;17(3B):1783-95.
Krivokapich et al., 13N Ammonia Myocardial Imaging at Rest and With Exercise in Normal Volunteers, Quantification of Absolute Myocardial Perfusion With Dynamic Positron Emission Tomography. Circulation. 1989; 80(5):1328-37.
Kroemer, Mitochondria in cancer. Oncogene. Aug. 7, 2006;25(34):4630-2.
Latli et al., Photoaffinity radioligand for NADH:ubiquinone oxidoreductase: [SC3H2](trifluoromethyl)diazirinyl-pyridaben. J. Labelled Compounds Radiopharm. 1998;41(3):191-9.
Lazewatsky et al., Dosimetry of BMS747158, a novel 18F labeled tracer for myocardial perfusion imaging, in nonhuman primates at rest. J Nucl Med. 2009;49(Supplement 1):15p.
Lazewatsky J, Case J, Maddahi J, Berman D, Slomka P, O'Loughlin L, Quirke A, Washburn D., (2011) Relative defect radioactivity and perceived defect severity are proportional with flurpiridaz F18 PET myocardial perfusion imaging. J Nucl Med. 52 (Supplement 1):1115.
Lazewatsky J., M. J., Berman D., Bhat G., Sinha S., Devine M., (2010) Development of a method for the determination of dose ratio and minimum inter-injection interval for a one-day rest-stress protocol with BMS747158 PET myocardial perfusion agent. Journal of Nuclear Medicine 51(Supplement 2):600.
Lindell et al., The design and synthesis of novel inhibitors of NADH: ubiquinone oxidoreductase. Bioorganic & Medicinal Chemistry Letters. 2004;14:511-4.
Liu et al., Integrin avb3 directed radiopharmaceuticals for tumor imaging. Drugs of the Future. 2003 ;28(6):551-64.
Maddahi et al., First human study of of BMS747158, a novel F-18 labeled tracer for myocardial perfusion imaging. J Nucl Med. 2008;49:70P.
Maddahi J, Berman D, Taillefer R, Udelson R, Devine M, Lazewatsky J, Bhat G and Washburn D., (2011) Phase 2 clinical comparison of flurpiridaz F 18 injection PET and SPECT myocardial perfusion imaging for diagnosis of coronary artery disease. J Nucl Med. 52 (Supplement 1):59.
Maddahi J, Berman D.S., Taillefer R., Udelson J., Devine M, Lazewatsky J., Bhat G, Washburn D.,(2011) Phase 2 safety and clinical comparison of flurpiridaz F18 injection PET and SPECT myocardial perfusion imaging for diagnosis of coronary artery disease. European Heart Journal Supplements ;13( Supplement A ): A45. Abstract # 197.
Maddahi J., (2012). Properties of an ideal PET perfusion tracer: New PET tracer cases and data. Journal of Nuclear Cardiology. 19(Supplement 1): S30-37.
Maddahi J., B. F., Huang H., Czernin J., Schelbert H., Zhu Q., Lazewatsky J., Case, JA., Sparks R., Phelps ME.,, J. Czernin, et al., (2011). Phase I, First-in-Human Study of BMS747158, a Novel 18F-Labeled Tracer for Myocardial Perfusion PET: Dosimetry, Biodistribution, Safety, and Imaging Characteristics After a Single Injection at Rest. J Nucl Med 52: 1-9.
Maddahi J., C. J., Ehlgen A., Lazewatsky J., Zhi Q., Phelps M., (2010). Comparison of F-18 labeled BMS747158 PET and Tc-99m labeled spect myocardial perfusion imaging for detection and evaluation of coronary artery disease. Journal of the American College of Cardiology 55(10A): E616.
Maddahi J., Czernin J, Berman D, Taillefer R, Devine M, Lazewatsky J, Bhat G and Washburn D., (2011) Comparison of flurpiridaz F 18 PET injection and Tc-99m labeled SPECT myocardial perfusion imaging for identifying severity and extent of stress induced myocardial ischemia in phase 2 clinical trials. J Nucl Med. 52 (Supplement 1):444.
Maddahi J., Huang. S., Truong D., Lazewatsky JL, Ehlgen A., Schelbert H., Dzernin J, Phelps M (2010). Preliminary results of absolute quantification of rest and stress myocardial blood flow with Flurpridaz F-18 PET in normal and coronary artery disease patients in a single-center study. Journal of Nuclear Cardiology 17(4): 743. Abstract # 31.18.
Maddahi J., L. M., Czernin C., Ehgen A., Lazewatsky J., Devine M., (2010) F-18 labeled BMS747158 PET myocardial perfusion imaging identifies more severe and extensive stress induced myocardial ischemia than Tc-99m Sestamibi SPECT. Journal of Nuclear Medicine 51(Supplement 2): 1739.
Maddahi, J; Bengel, F; Huang, H; Czernin, J; Schelbert, H; Zhu, Q; Lazewatsky, J; Case, JA; Sparks, R; Phelps, ME., Phase 1 Human safety, dosimetry, Biodistribution and rest/stress myocardial imaging characteristics of F18 Labeled BMS 747158. (2009) Journal of the American College of Cardiology 53(10): A297. Abstract #1054-263.
Maddahi, J; Huang, H, Schiepers, C; Schelbert, H; Wijatyk, A; Lazewatsky, J; Zhu, Q; Phelps, M., (2009) Protocols for same day rest-stress PET imaging with the new F-18 labeled BMS747158 myocardial perfusion tracer. European Heart Journal;11(Supp B): S89. Abstract #433.
Maddahi, J; Huang, H; Czernin, J; Schelbert, H; Bengel, F; Wijatyk, A; Lazewatsky, J; Zhu, Q., (2009) Human safety, dosimetry,

(56) References Cited

OTHER PUBLICATIONS biodistribution, and rest-stress myocardial imaging characteristics of the new F-18 labeled BMS747158 myocardial perfusion PET tracer. European Heart Journal 11(Supplement): S89. Abstract #432.
Maddahi, J; Huang, S; Schiepers, C; Bengel, F; Czernin, J; Schelbert, H; Lazewatsky, J; Zhu, Q; Phelps, ME., (2009) Same day rest-stress protocols for PET imaging with the new F-18 labeled BMS747158 myocardial perfusion tracer. Journal of Nuclear Medicine 50(Supplement 2): 1173.
Magerstadt et al., Gd(DOTA): An Alternative to Gd(DTPA) as a T1,2 Relaxation Agent for NMR Imaging of Spectroscopy. Magnetic Resonance in Medicine. 1986; 3:808-12.
Marshall et al., Kinetic Analysis of a $^{125}$I-iodorotenone as a deposited myocardial flow tracer: Comparison with $^{99m}$Tc-sestamibi. Journal of Nuclear Medicine. 2001; 42(2): 272-81.
Marshall et al., Kinetic Analysis of a $^{18}$F-fluorodihydrorotenone as a deposited myocardial flow tracer: Comparison with $^{291}$T1. Journal of Nuclear Medicine. 2004;45(11):1950-9.
Martarello et al., Synthesis and evaluation of a new fluorine-18 labeled rotenoid as a potential pet probe of mitochondrial complex I activity. Journal of Labelled Compounds and Radiopharmaceuticals. 1999;42(11):1039-51.
Miller et al., Synthesis of 11C, 18F, 15O, and 13N radiolabels for positron emission tomography. Angew Chem Int Ed Engl. 2008;47(47):8998-9033.
Mistry et al., Toxicological evaluation of BMS-747158, a PET myocardial perfusion imaging agent. The Toxicologist. 2008;102:476.
Miyoshi et al., Essential structural factors of annonaceous acetogenenins as potent inhibitors of mitochondrial complex I. Biochimica et Biophysica Acta. 1998;1365(3):443-52.
Miyoshi, Structure-activity relationships of some complex I inhibitors. Biochim Biophys Acta. May 6, 1998;1364(2):236-44.
Mou et al., Preparation and biodistribution of [18F]FP2OP as myocardial perfusion imaging agent for positron emission tomography. Bioorg Med Chem. Feb. 2010;18(3):1312-20. Epub Dec. 26, 2009.
Nakanishi et al., Acetogenins as selective inhibitors of the human ovarian 1A9 tumor cell line. Journal of Medicinal Chemistry. 2003;46(15):3185-8.
Nekolla et al., Assessment of imaging properties of a new F-18 labelled flow tracer in a pig model. J Am Coll Cardiol. 2008;51:A170.
Nekolla et al., Evaluation of the novel myocardial perfusion positron-emission tomography tracer 18F-BMS-747158-02: comparison to 13N-ammonia and validation with microspheres in a pig model. Circulation. May 5, 2009;119(17):2333-42. Epub Apr. 20, 2009.
Nekolla S, Sibylle R, Higuchi T, Saraste A, Yu M, Robinson S, Casebier D and Schwaiger M., Evaluation of a new myocardial PET tracer 18F-BMS-747158-02 (18F-BMS): Comparison to 13N ammonia and validation with microspheres. J Nucl Med. 2008; 49 (Supplement 1):29P.
Nekolla S.G., Saraste A.., (2011). Novel F-18 Labeled PET Myocardial Perfusion Tracers: Bench to Bedside. Current Cardiology Reports 13: 145-150.
Nicolaou et al., Combinatorial synthesis of novel and potent inhibitors of NADH: ubiquinone oxidoreductase. Chemistry & Biology. 2000;7:979-92.
Okun et al., Three classes of inhibitors share a common binding domain in mitochondrial complex I (NADH:ubiquinone oxidoreductase). J Biol Chem. Jan. 29, 1999;274(5):2625-30.
Pauwels et al., Fluorine-18-radiolabeled pharmaceuticals for imaging with positron emission tomography, excluding [18F]-fluorodeoxyglucose. Drugs of the Future. 2002; 27:655-67.
Purohit et al., Quinazoline derivatives as MC-I inhibitors: evaluation of myocardial uptake using Positron Emission Tomography in rat and non-human primate. Bioorg Med Chem Lett. Sep. 1, 2007;17(17):4882-5. Epub Jun. 14, 2007.
Purohit et al., Synthesis and biological evaluation of pyridazinone analogues as potential cardiac positron emission tomography tracers. J Med Chem. May 22, 2008;51(10):2954-70. Epub Apr. 19, 2008.
Radeke et al., Synthesis and biological evaluation of the mitochondrial complex 1 inhibitor 2-[4-(4-fluorobutyl)benzylsulfanyl]-3-methylchromene-4-one as a potential cardiac positron emission tomography tracer. J Med Chem. Sep. 6, 2007;50(18):4304-15. Epub Aug. 15, 2007.
Ravert et al., Radiosynthesis of 3-[$^{18}$F]fluoropropyl and 4-[18F]fluorobenzyl triarylphosphonium ions. J Lab Comp Radiopharm. 2004;47(8):469-76.
Ritchie et al., Guidelines for clinical use of cardiac radionuclide imaging. Report of the American College of Cardiology/American Heart Association Task Force on Assessment of Diagnostic and Therapeutic Cardiovascular Procedures (Committee on Radionuclide Imaging), developed in collaboration with the American Society of Nuclear Cardiology. J Am Coll Cardiol. Feb. 1995;25(2):521-47.
Runge et al., MR Imaging of Rat Brain Glioma: GD-DTPA versus GD-DOTA. Radiology. 1988;166(3):835-8.
Santi et al., Toxicology of rotenone. Farmaco Sci. Apr. 1965;20:270-9.
Schelbert et al., N-13 ammonia as an indicator of myocardial blood flow. Circulation. Jun. 1981;63(6):1259-72.
Schuler et al., Functional coupling of PSST and ND1 subunits in NADH: ubiquinone oxidoreductase established by photoaffinity labeling. Biochimica et Biophysica Acta. 2001;1506:79-87.
Schlyer, PET tracers and radiochemistry. Ann Acad Med Singapore. Mar. 2004;33(2):146-54.
Sherif H, N. S., Saraste A., Reder S., Yu M., Robinson S, Schwaiger M, (2011). Simplified quantification of myocardial flow reserve with flurpiridaz F-18: Validation with Microspheres in a pig model. Journal of Nuclear Medicine 52: 617-624.
Sherif H, Saraste A, Higuchi T, Reder S, Weidl E, Poethko T, Weber A, Robinson S, Nekolla S, and Schwaiger M. Evaluation of the novel PET perfusion tracer 18F BMS747158-02 for measurement of myocardial infarct size in a rat model. J Nucl Med. 2008; 49 (Supplement 1):186P.
Sherif H. Nekolla SC. Schwaiger M, (2011). Reply: Simplified Quantification of Myocardial Flow Reserve with 18F-Flurpiridaz: Validation with Microspheres in a Pig Model. Journal of Nuclear Medicine 52(11): 1835-1836.
Sherif HM, Saraste A, Weidl E, Weber AW, Higuchi T, Reder S, Poethko T, Henriksen G, Casebier D, Robinson S, Wester HJ, Nekolla SG, Schwaiger M, Evaluation of a novel (18)F-labeled positron-emission tomography perfusion tracer for the assessment of myocardial infarct size in rats. Circulation: Cardiovascular Imaging. Mar. 2009;2(2):77-84.
Slomka PJ, M. J. L. M. L., Lazewatsky JL, Germano G., Berman DS, (2010) Multicenter development of normal perfusion and function limits for stress and rest flurpiridaz F-18 Cardiac PET. Journal of Nuclear Cardiology 17(4): 725. Abstract #9.14.
Soderquist et al., Reductive cleavage of acetals and ketals with 9-borabicyclo[3.3.1]nonane†. Org Process Res Dev. 2006;10(5):1076-9.
Talpade et al., In vivo labeling of mitochondrial complex I (NADH:ubiquinone oxidoreductase) in rat brain using [(3)H]dihydrorotenone. J Neurochem. Dec. 2000;75(6):2611-21.
Tamarappoo B.K, N. R., Hayes S.W, Thomson L.E.J, Friedman J.D, Cheng V.Y, Slomka P.J, Kim J., Gransar H., Germano G., Ehlgen A., Berman D.S, (2010) Comparison of myocardial stress perfusion defect assessment using 99mTc Sestamibi SPECT vs 18F-BMS747158 PET. Journal of Nuclear Cardiology 17(4): 742. Abstract #31.14.
Ueno et al., Comparison of the inhibitory action of natural rotenone and its stereoisomers with various NADH-ubiquinone reductases. Eur J Biochem. Oct. 1, 1994;225(1):411-7.
Unger, Pesticide synthesis handbook. Technology and Engineering. 1996:523-4. Google books result.

(56) References Cited

OTHER PUBLICATIONS

Vanbrocklin et al., (F-18)fluorodihydrorotenone: Synthesis and evaluation of a mitochondrial electron transport chain (ETC) complex I probe for PET. Journal of Nuclear Medicine. 1994; 35(5 Suppl):73P.

Vanbrocklin et al., Fluorine-18 labeled dihydrorotenone analogs: preparation and evaluation of PET mitochondrial probes. Journal of Labelled Compounds and Radiopharmaceuticals, Symposium abstracts (continue in part IV). 1994; 35:217-19.

Vanbrocklin et al., Mitochondrial avid radioprobes. Preparation and evaluation of 7'(Z)-[125I]iodorotenone and 7'(Z)-[125I]iodorotenol. Nucl Med Biol. Jan. 2007;34(1):109-16. Epub Nov. 28, 2006.

Walker, The NADH: ubiquinone oxidoreductase (complex I) of respiratory chains. Quarterly Review of Biophysics. 1992;25(3):253-324.

Wallace, A mitochondrial paradigm of metabolic and degenerative diseases, aging, and cancer: a dawn for evolutionary medicine. Annu Rev Genet. 2005;39:359-407.

Wang et al., Insights into amyloid-beta-induced mitochondrial dysfunction in Alzheimer disease. Free Radic Biol Med. Dec. 15, 2007;43(12):1569-73. Epub Sep. 21, 2007.

Woo J, Tamarappoo B, Dey D, Nakazato R, Le Meunier L, Ramesh A, Lazewatsky J, Germano G, Berman DS, Slomka PJ., (2011). Automatic 3D registration of dynamic stress and rest (82)Rb and flurpiridaz F 18 myocardial perfusion PET data for patient motion detection and correction. Medical Physics 38(11): 6313-26.

Yalamanchili et al., Mechanism of uptake and retention of F-18 BMS-747158-02 in cardiomyocytes: a novel PET myocardial imaging agent. J Nucl Cardiol. Nov.-Dec. 2007;14(6):782-8. Epub Oct. 22, 2007.

Yu et al., Assessment of 18F-labeled mitochondrial complex I inhibitors as PET myocardial perfusion imaging agents in rats, rabbits, and primates. Eur J Nucl Med Mol Imaging. Jan. 2009;36(1):63-72. Epub Aug. 21, 2008.

Yu et al., BMS-747158-02: a novel PET myocardial perfusion imaging agent. Journal of Nuclear Cardiology. 2007;14(6):789-98.

Yu et al., Evaluation of LMI1195, a Novel 18F-Labeled Cardiac Neuronal PET Imaging Agent, in Cells and Animal Models. Circulation: Cardiovascular Imaging 2011 4: 435-443.

Yu et al., The next generation of cardiac positron emission tomography imaging agents: discovery of flurpiridaz f-18 for detection of coronary disease. Seminars Nucl Med. Jul. 2011;41(4):305-13.

Yu M, Guaraldi M, Kagan M, Azure M. and Robinson R., Cardiac imaging and uptake of BMS747158-02 under various experimental conditions. J Nucl Med. 2008; 49 (Supplement 1):187P.

Yu M, Guaraldi M, Kagan M, McDonald J., Hayes M., Yalamanchili P, Mistry M, Radeke H, Azure M, Casebier D, Robinson S,., Myocardial Perfusion Imaging with 18F-Chromone Based MC-1 Inhibitors. Molecular Imaging. 2006;5(3):372-3. Abstract ID: 642 Poster board space:105.

Yu M, Mistry M, Guaraldi M, Kagan M, McDonald J., Drew K, Hayes M, Yalamanchili P, Purohit A, Radeke H, Azure M, Hanson K, Robinson S, Casebier D., [18F]-RP1012: A Novel Myocardial Perfusion Imaging Agent for use with positron emission tomography (PET). Circulation Supplmement 2, 112(17), II-761, Abstract #3546, 2005.

Yu M, Yalamanchili P., Purohit A, Radeke H, Azure M, Mistry M, Hayes M, Hanson K, Guaraldi M, Drew K, McDonald J, Wexler E, Su F., Benetti R, Casebier D, Robinson S., In-vivo Assessment of Mitochondrial Complex-1 Inhibitors as Myocardial Perfusion Imaging Agents (MPIA). Circulation Supplement 2, 112 (17), II-474, Abstract #2283, 2005.

Yu M, Bozek J, Guaraldi M, Kagan M, Azure M, Robinson SP., Cardiac imaging and safety evaluation of BMS747158, a novel PET myocardial perfusion imaging agent, in chronic myocardial compromised rabbits. J Nuclear Cardiology. 2010;17(4):631-6.

Yu M, Guaraldi M.T, Bozek J, Kagan M, Azure M, Radeke Cdebaca M.H, Robinson S.P., Effects of Food Intake and Anesthetic on Cardiac Imaging and Uptake of BMS-747158-02 in Comparison with FDG. Journal Nuclear Cardiology. Sep.-Oct. 2009;16(5):763-8.

Yu M, Robinson S.P. A novel cardiac PET imaging agent. International Hospital Equipment and Solutions. 2009; 35(4):14-5.

International Preliminary Report on Patentability for PCT/US2006/031231, mailed Feb. 21, 2008.

International Search Report and Written Opinion for PCT/US2006/031231, mailed Mar. 15, 2007.

International Preliminary Report on Patentability for PCT/US2009/001296, mailed Sep. 10, 2010.

International Search Report and Written Opinion for PCT/US2009/001296, mailed Sep. 30, 2009.

International Preliminary Report on Patentability for PCT/US2009/001247, mailed Sep. 10, 2010.

International Search Report and Written Opinion for PCT/US2009/001247, mailed Oct. 21, 2009.

International Search Report and Written Opinion for PCT/US2010/001120, mailed Dec. 28, 2010.

International Preliminary Report on Patentablitiy for PCT/US2010/001120, mailed Oct. 27, 2011.

International Search Report and Written Opinion for PCT/US2011/024109, mailed Oct. 24, 2011.

Extended European Search Report for EP 10764772.9 mailed May 8, 2015.

* cited by examiner

STABILIZATION OF RADIOPHARMACEUTICAL COMPOSITIONS USING ASCORBIC ACID

RELATED APPLICATIONS

This application is a national stage filing under 35 U.S.C. §371 of International Application No. PCT/US2010/001120, filed Apr. 15, 2010, which was published under PCT Article 21(2) in English, and which claims priority under 35 U.S.C. §119 from U.S. Provisional Application Ser. No. 61/169,353, filed Apr. 15, 2009, the entire contents of both of which are incorporated by reference herein.

FIELD OF THE INVENTION

The present invention is directed to the stabilization of radiopharmaceutical compositions, and the protection thereof from radiolytic and propagative radical decomposition. In particular, the invention is directed to the use of an antioxidant species in a radiopharmaceutical formulation via buffering of the composition. The invention moreover is concerned with the use of the antioxidant ascorbic acid, under buffered conditions in a particular pH range, to stabilize a radiopharmaceutical composition useful for medical imaging, and thereby enhance the shell life of the composition, while maintaining the composition as suitable for administration to a human, and other mammalian subjects.

BACKGROUND OF THE INVENTION

Radiopharmaceuticals are drugs containing a radionuclide. Radiopharmaceuticals are used routinely in nuclear medicine for the diagnosis or therapy of various diseases. They are typically small organic or inorganic compounds with a definite composition. They can also be macromolecules, such as antibodies or antibody fragments that are not stoichiometrically labeled with a radionuclide. Radiopharmaceuticals form the chemical basis for the diagnosis and therapy of various diseases. The in vivo diagnostic information can be obtained by intravenous injection of the radiopharmaceutical and determination of its biodistribution using a gamma camera or a PET camera. The biodistribution of the radiopharmaceutical typically depends on the physical and chemical properties of the radiolabeled compound and can be used to obtain information about the presence, progression, and state of disease.

Radiopharmaceuticals can generally be divided into two primary classes: those whose biodistribution is determined exclusively by their chemical and physical properties, and those whose ultimate distribution is determined by their receptor binding or other biological interactions. The latter class is often described as being target-specific.

Recently, much effort has been expended on the discovery and development of radiopharmaceuticals for diagnostic imaging which contain positron emitting isotopes. Positron emitting isotopes include $^{82}$Rb, $^{124}$I, $^{11}$C, $^{13}$N, and $^{18}$F, among others. These isotopes decay by the emission of a positron from the nucleus. A positron is a particle that has an equivalent mass of an electron, but a corresponding positive charge. The positron, after ejection from the nucleus, travels until it encounters an electron, and the reaction of the two masses results in a physical annihilation of the masses. Energy released in opposing directions at a value of 511 kEv, and because the annihilation has no angular momentum, the photons are projected from the point of annihilation approximately 180 degrees apart, allowing for precise determination of a line along which the said decomposition occurred. This property results in exquisite sensitivity and resolution, and allows for superb image reconstruction and quality.

An advantage of the carbon, nitrogen and fluorine isotopes is that they may be incorporated into small organic molecules, such as known or investigational pharmaceuticals that could be used to determine biodistribution of the agent, as well as diagnose the presence, absence or extent of disease. They may conveniently be inserted into these molecules by a variety of methods known to organic chemists and radiochemists ordinarily skilled in the art. Widespread use in investigational research has been made of $^{11}$C-methyl iodide ($^{11}$CH$_3$I), methylating an alcohol or an amine to produce the corresponding ether or alkyl amine. These compounds are then appropriately sterilized, formulated and injected into a subject.

The primary drawback to the widespread use of many PET radiopharmaceuticals is the relatively short half lives associated with many of the isotopes. Rubidium-82, carbon-11, and nitrogen-13 have half-lives of 1.27, 20.3, and 9.97 minutes, respectively. Rubidium is administered as the chloride salt from a $^{82}$Sr—$^{82}$Rb generator, and is not synthetically modified or manipulated. Nitrogen-13 is typically administered as ammonia ($^{13}$NH$_3$) produced in a cyclotron adjacent to an imaging center with appropriate proximity to a camera. Both $^{11}$C- and $^{13}$N-based reagents have been used in the radiolabeling of imaging agents. Significant engineering and logistical challenges need to be met to allow for the use of the compounds as radiopharmaceuticals given the short half life and the necessary time to accomplish the required reactions and purification prior to formulation and administration of the drug.

Correspondingly longer-lived positron emitting isotopes may be incorporated into new radiotracers for imaging. These include the aforementioned $^{131}$I and $^{18}$F, with half-lives of 4.2 days and 107.9 minutes, respectively. The most prevalent use of late has been $^{18}$F, as the decay is entirely through the emission of positrons and has a favorable half life. The approximate two hours allows for synthetic incorporation into a molecule, purification and subsequent distribution from a centrally located radiopharmacy, obviates the requirement/investment in either an on-site cyclotron or the monthly purchase of a $^{82}$Sr—$^{82}$Rb generator.

During the course of manufacture, formulation, release, and delivery of doses, the isotope typically decays at a zero-order rate dictated by the physics of each particular isotope. However, this decay can also trigger chemical decay of the dose, by radiolysis. This can propagate via radical reaction and seriously diminish the quality of the composition.

Decomposition of the radiopharmaceutical composition prior to or during administration can dramatically decrease the targeting potential and increase the toxicity of the therapeutic radiopharmaceutical composition. Thus, in some cases, it is important to ensure that the radionuclide is linked to the targeting moiety, and to further ensure that specificity of the targeting agent is preserved.

Radiolysis is caused by the formation of free radicals such as hydroxyl and superoxide radicals (Garrison, W. M. *Chem. Rev.* 1987, 87, 381-398). Free radicals are very reactive towards organic molecules. The reactivity of these free radical towards organic molecules can affect the solution stability of a radiopharmaceutical composition. Stabilization of the radiopharmaceutical composition is a recurrent challenge in the development of target-specific radiopharmaceuticals, and radical scavengers are often employed as a stabilizer to minimize radiolysis of the radiolabeled molecules. Some stabilizers are "radical scavenging antioxidants" that readily react with hydroxyl and superoxide radicals. The stabilizing agent for radiopharmaceutical compositions may advantageously possess the following characteristics: low or essentially no toxicity when it is used for human administration, low or essentially no interference with the delivery or receptor binding of the radiolabeled compound to the target cells or tissue(s), and/or the ability to stabilize the radiopharmaceutical for a reasonable period of time (e.g., during the preparation, release, storage and transportation of the radiopharmaceutical).

Radical scavengers such as ascorbic acid have been used to stabilize $^{99m}$Tc (DeRosch, et al, WO95/33757) and $^{186/188}$Re (*Anticancer Res.* 1997, 17, 1783-1796) radiopharmaceuticals. U.S. Pat. No. 5,393,512 discloses the use of ascorbic acid as a stabilizing agent for $^{186}$Re and $^{131}$I-labeled antibodies or antibody fragments. U.S. Pat. Nos. 5,093,105 and 5,306,482 disclose the use of ascorbic acid as an antioxidant for $^{99m}$Tc radiopharmaceuticals.

Several strategies have been developed for the use of antioxidants such as ascorbic acid to terminate decay pathways prior to significant damage occurring. Ascorbic acid has been used in various pharmaceutical and radiopharmaceutical compositions. Unlike other buffering agents such as succinic acid and aminocarboxylates, ascorbic acid contains no amino or carboxylic groups. PCT/US94/06276 discloses stabilizing agents such as ascorbic acid and water soluble salts and esters of ascorbic acid.

U.S. Pat. No. 6,066,309 discloses the use of ascorbic acid and derivatives thereof in stabilizing radiolabeled proteins and peptides against oxidative loss of radiolabels and autoradiolysis. In some cases, ascorbic acid is added after radiolabeling, including any required incubation period, but prior to patient administration. In addition, derivatives of ascorbic acid are defined as salts of ascorbic acid, esters of ascorbic acid, or mixtures thereof.

Although the use of ascorbic acid/ascorbate as a stabilizer has been disclosed for a variety of diagnostic and therapeutic radiopharmaceutical compositions (see, e.g., Deausch, E. A. et al./U.S. Pat. No. 5,384,113/1995; Vanderheyden, J.-L., et al./U.S. Pat. No. 5,393,512/1995; Flanagan, R. J. and Tartaglia, D./U.S. Pat. No. 5,093,105/1992; Tartaglia, D. and Flanagan, R. J./U.S. Pat. No. 5,306,482/1994; Shochat, D. et al./U.S. Pat. No. 5,961,955/1999; and Zamora, P. O. and Merek, M. J./U.S. Pat. No. 6,066,309/2000), there has been little or no disclosure regarding the use of ascorbate within a specified range of pH to enhance the antioxidant action of the compound for clinical applications.

While significant use of antioxidants such as ascorbic acid have been exemplified in the literature, little attention has been paid to the state of the antioxidant, e.g., as when adding it into a buffered solution for stability studies at low pH or at higher pH for material suitable for injection.

Material suitable for injection in humans may be selected to have a pH higher than 4.0 to reduce the risk of localized irritation and pain associated with a strongly acidic solution at an injection site. Typically, solutions for injection have been buffered by phosphate (phosphate buffered saline (PBS)) in the pH range of 6-8. However, the employment of ascorbic acid/ascorbate in buffered solutions at typical biological pH ranges (6-8) often exhibits a lower ability to stabilize radiopharmaceutical solutions. Conversely, while previous work may demonstrate stability of radiopharmaceutical preparations using ascorbic acid at low pH values (2-3), such formulations are generally not suitable for use in animal models or humans due to localized reactions, as noted above. In addition, previous work may set forth a broad acidic pH range for the ascorbic acid than is useful, or specify no particular range at all. To date, it is believed that there has been little guidance for the skilled artisan in selecting pH when using ascorbic acid for clinical applications of radiopharmaceuticals.

Accordingly, improved compositions and methods are needed.

SUMMARY OF THE INVENTION

The present invention provides for the use of ascorbic acid as a stabilizer in a pH range. The agents and stabilizers are formulated in ethanol-aqueous or aqueous buffer such that the solution is preferably in the acidic pH range of about 3.5-5.5, more preferably in the range of about 4-5, and most preferably in the range of about 4-4.5.

Thus, in some embodiments, the invention provides a composition, comprising one or more radiopharmaceutical compounds, together with a stabilizer comprising ascorbic acid, wherein the pH of said composition is within the range of about 3.5-5.5. The radiopharmaceutical compounds as part of the composition of the invention may be selected from the group consisting of rotenone, pyridaben, fenazaquin, fenpyroximate, tebufenpyrad, piericidins, and 2-substituted chromones, and analogs thereof. In some embodiments, said radiopharmaceutical compound is at least one member selected from the group consisting of pyridaben and analogs thereof. In some embodiments, said radiopharmaceutical compound is at least one member selected from the group consisting of compounds containing a 2-alkyl-4-chloro-2H-pyridazin-3-one with a lipophilic side chain substituted at the 5-position. In some embodiments, said radiopharmaceutical compound is 2-tert-Butyl-4-chloro-5-[4-(2-[$^{18}$F]fluoro-ethoxymethyl)-benzyloxy]-2H-pyridazin-3-one.

In some embodiments, said radiopharmaceutical compound is labeled with a radioisotope, such as a radioisotope is selected from the group consisting of $^{11}$C, $^{13}$N, $^{18}$F, $^{86}$Br, $^{124}$I, $^{125}$I and $^{131}$I. In some embodiments, said radioisotope is selected from the group consisting of $^{11}$C, $^{13}$N, and $^{18}$F. In some embodiments, said radioisotope is $^{18}$F.

In any of the foregoing embodiments, the radiopharmaceutical composition comprises between about 5 and 100 mg/mL of ascorbic acid, more preferably between about 25 and 500 mg/mL, and more preferable between about 50 and 200 mg/mL. In some embodiments, there is greater than about 5 mg, greater than about 10 mg, greater than about 20 mg, greater than about 30 mg, greater than about 40 mg, greater than about 50 mg, greater than about 100 mg, or greater than about 200 mg of ascorbic acid per milliliter.

The invention also provides a method for preparing a composition as described in any of the foregoing embodiments, which comprises adding a first solution containing a radiopharmaceutical compound to a second solution containing ascorbic acid within the pH range of about 3.5-5.5, more preferably within the range of about 4-5, and even more preferably within the range of about 4-4.5, to form a third solution comprising the radiopharmaceutical compound and ascorbic acid. In some embodiments, the radiopharmaceutical compound is purified by chromatography, prior to addition of the first solution to the second solution. In some embodiments, the radiopharmaceutical compound is not purified by chromatography, prior to addition of the first solution to the second solution. In some embodiments, the method further comprises the step of adjusting the pH of the third solution to about 6-8, after addition of the first solution to the second solution and prior to using the composition in a patient.

Further as part of the invention there is a method which comprises administering to a patient a radiopharmaceutical composition containing ascorbic acid, such that the composition has a pH within the range of about 3.5-5.5, more preferably within the range of about 4-5, and even more preferably within the range of about 4-4.5.

The present invention is directed to these, as well as other important ends, hereinafter described.

DETAILED DESCRIPTION OF THE INVENTION

Figure 1:
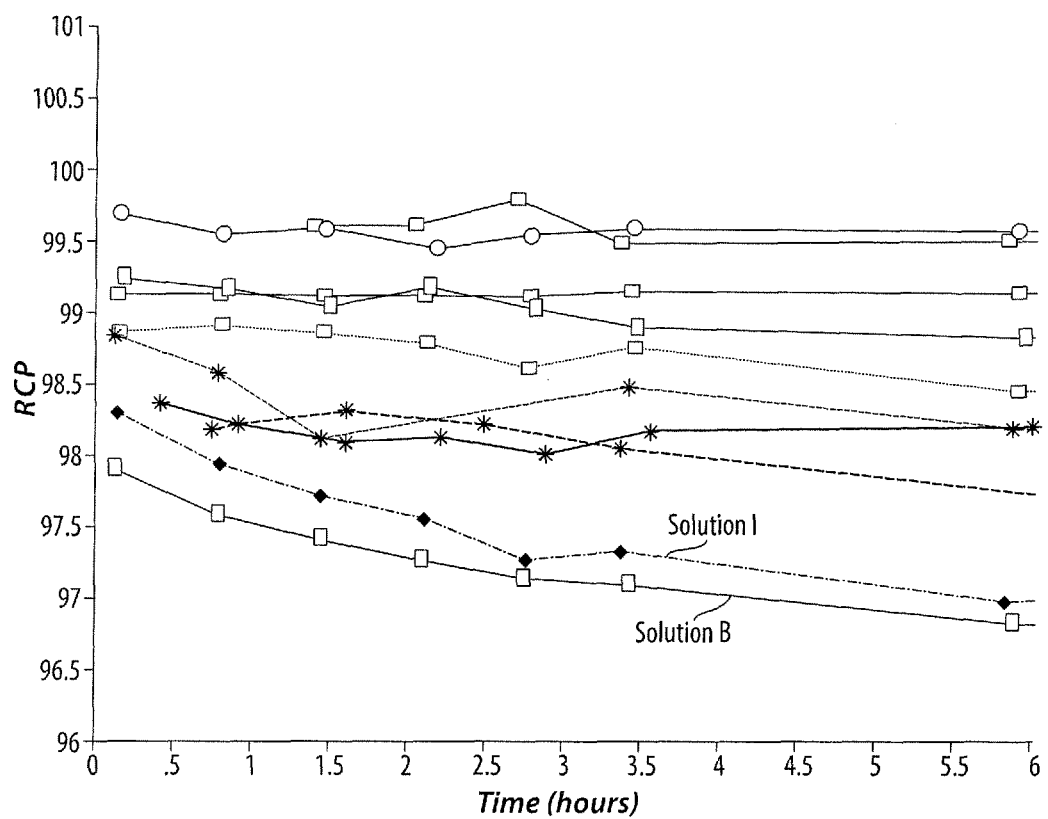
FIG. 1 shows a plot of radiochemical purity of various compositions of the invention, as a function of time.

There are several advantages to using ascorbic acid as a buffering agent. Ascorbic acid has been approved for pharmaceutical and radiopharmaceutical applications. Ascorbic acid has a pKa of 4.2 and has buffering capacity at pH 3.0-5.0. At higher concentrations (>50 mg/mL or 0.25 M), it may also have sufficient buffering capacity at the pH range 5.5-6.0, or higher. Typically, it is also employed as a primary buffer.

The invention is generally directed to novel compositions (e.g., radiopharmaceutical compositions), and to the unforeseen and dramatic increase in the antioxidant capacity and stabilizing effect of the antioxidant ascorbic acid in the radiopharmaceutical compositions at a certain pH range. At this pH, a significant portion of the antioxidant is protonated, yet the acidity of the solution is not so great to cause a severe reaction in the subject. It is particularly suitable to perform manufacturing and storage protocols under the conditions described herein, and adjusting to a higher pH within 5, 10, or 15 minutes of administration to a subject. In some embodiments, radiotracers (e.g., $^{18}$F-labeled radiotracers) utilizing ascorbic acid as a stabilizing agent and/or as a clinical PET imaging agent are provided.

The invention advantageously provides radiopharmaceutical formulations which utilize ascorbic acid as a stabilizer within a certain pH range. The pH range enhances the stability and shelf-life of the composition while minimizing severe localized site reactions upon injection. In addition, some embodiments utilize ascorbic acid as a stabilizing agent for the preparation of labeled molecules, in particular $^{18}$F-labeled molecules, in radiopharmaceutical compositions. In some cases, ascorbic acid and its analogs, within a certain pH range, can serve as a stabilizer during preparation, release, and transportation of the radiopharmaceutical composition, and in particular for those compounds which are labeled with radioisotopes such $^{18}$F.

The pH of the radiopharmaceutical compositions is selected to lie at or near the pKa of either the primary or, in the case of dibasic ions, the secondary pKa of the antioxidant. For ascorbic acid, with a pK of 4.17, the pH may be selected to be in the range of about 3.5-5.5, about 4-5, or 4-4.5.

Ascorbic acid is typically utilized as a stabilizing component of the radiopharmaceutical composition of the invention. Ascorbic acid is known as vitamin C, and has been used as an antioxidant to prevent radiolytic decomposition of certain radiopharmaceuticals (WO95/33757; *Anticancer Res.* 1997, 17, 1783-1796; U.S. Pat. No. 5,093,105, and U.S. Pat. No. 5,306,482) or radiolabeled peptides (U.S. Pat. No. 5,393,512; U.S. Pat. No. 5,384,113 and U.S. Pat. No. 5,961,955). As used herein, the term "ascorbic acid" includes ascorbic acid itself as well as analogs and salts of the acid known to those of ordinary skill in the art. Ascorbic acid is readily available GRAS (generally recognized as safe) substance and can be used in pharmaceutical compositions and other formulations used for biological purposes, at levels as high as 200 mg/mL of the final formulation. Previous compositions including ascorbic acid were typically at pH values within biological pH range (e.g., 6-8) during essentially all processing steps, as well as administration to a subject, to reduce the risk of irritation and pain associated with acidic solutions. However, within biological pH range, the ability of ascorbic acid/ascorbate in buffered solutions to stabilize radiopharmaceutical solutions is surprisingly reduced.

Some advantages of using ascorbic acid or its analogs in a radiopharmaceutical composition disclosed in this invention include: (1) the ability to prepare radiopharmaceutical compositions in high yield (>90%) and (2) the ability to store the radiopharmaceutical compositions for several hours or even days, while maintaining the radiochemical purity or RCP (>90%) of the radiopharmaceutical. In some cases, ascorbate salts may be added to the formulation. In some cases, ascorbic acid may be used in the uncharged form, or in compositions in which a higher percentage of ascorbic acid is protonated at the appropriate pH. Without being bound by any particular theory, the efficacy of the antioxidant may, in some cases, be directly related to the non-ionic nature of the hydrogen-oxygen bonds in the antioxidant, with enhanced stability at acidity levels wherein a significant portion of the antioxidant is in protonated form.

In some embodiments, the radiopharmaceutical compositions may include ascorbic acid as a stabilizer, in the absence of other stabilizers compounds.

The invention contemplates radiopharmaceutical formulations containing one or more of the hereinafter described myocardial perfusion imaging agents or radiopharmaceutical compounds, together with ascorbic acid, in the pH range as heretofore set forth.

Recently, several series of novel myocardial perfusion imaging agents have been disclosed (Casebier, et al. U.S. 2007036716A1; Purohit & Casebier, U.S. 2006083681 A1; Radeke, et al. U.S. 2005244332A1; Casebier, et al. WO2005/079391A2) that have highly desirable properties for potential clinical diagnostic use. These agents are often prepared as radiotracers, and are often labeled with the radioisotopes, such as the radioisotope $^{18}$F.

Some radiopharmaceutical compounds useful in the invention can be potent inhibitors of mitochondrial complex 1 (MC-1), and have potential clinical utility. These compounds may be radiolabeled with a radiotracer (hereinafter described, such as $^{18}$F by way of illustration), and, therefore, stabilization of the solution in such a manner as to prevent radiolytic initiated decay may be desired. Several classes of compounds may be useful as radiopharmaceutical compounds within the context of the invention, as described more fully below.

For example, the natural product rotenone is a known commercial insecticide and is widely used in commerce. The primary mode of activity is via the inhibition of MC-1. The compound is convenient for crop use due to its potency as well as its rapid breakdown to benign products in the environment. Several analogs of rotenone are known to inhibit MC-1 and some have been used in non-human models of myocardial perfusion imaging, such as dihydrofluorotenone (DHFR), for example.

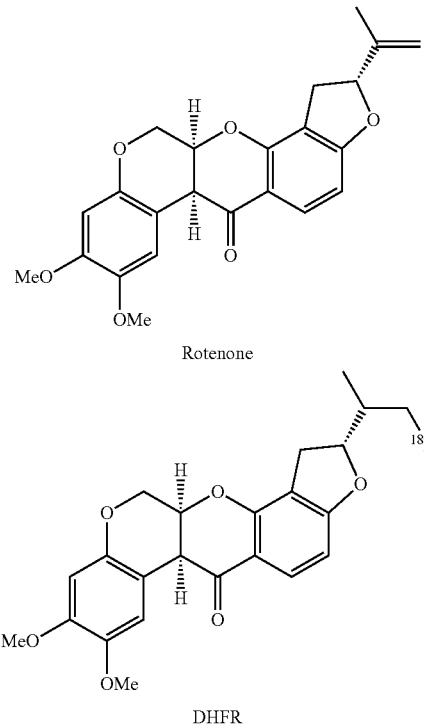

Rotenone

DHFR

Another compound class that may be used for myocardial perfusion imaging, and the solutions of which may be stabilized by ascorbic acid is a class of chromone derivatives shown below. These compounds are synthetic compounds that have shown good utility in myocardial perfusion in primates, especially the specific compound shown below.

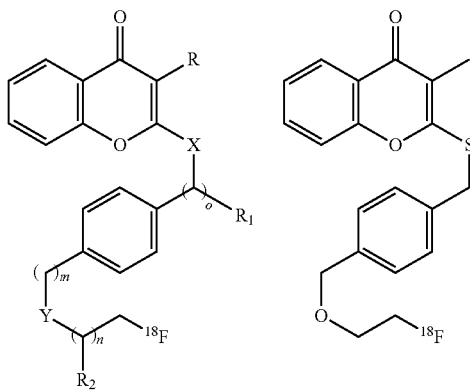

X = O, S, NR
Y = O, S, NR, $CH_2$
R = H, Me, Cl, $CH_2$$^{18}$F
m = 0, 1, 2, 3
n = 0, 1, 2, 3
o = 0, 1, 2 3,
$R_1$, $R_2$ = H, Alkyl Another compound class that may be used for myocardial perfusion imaging, and the solutions of which may be stabilized by ascorbic acid are derivatives of a quinalzoline called fenazquin. Fenazaquin itself is a strong inhibitor of MC-1 and is used commercially as an insecticide. Radiolabeled derivatives of fenazaquin and its analogs have shown good utility in imaging myocardium perfusion in primates and other mammals. Fenazaquin and its analogs are shown below, along with an especially preferred specific compound for myocardial perfusion imaging.

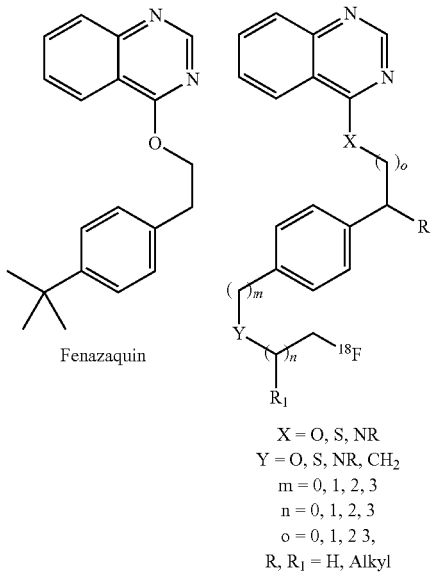

Fenazaquin

X = O, S, NR
Y = O, S, NR, $CH_2$
m = 0, 1, 2, 3
n = 0, 1, 2, 3
o = 0, 1, 2 3,
R, $R_1$ = H, Alkyl

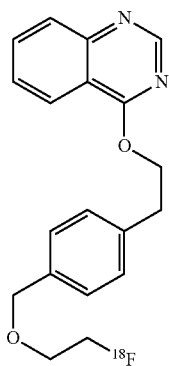

Similarly, analogs of other commercially useful MC-1 inhibitors are useful in this invention, such as tebufenpyrad and analogs thereof, as shown below. The parent structure of these compounds are commercially used as insecticides, but analogs of them may be radiolabeled for use as myocardial perfusion imaging agents.

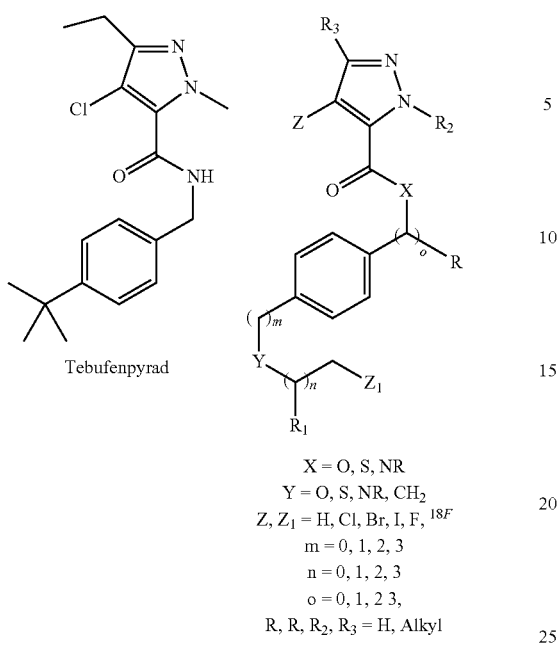

Tebufenpyrad

X = O, S, NR
Y = O, S, NR, CH$_2$
Z, Z$_1$ = H, Cl, Br, I, F, $^{18}F$
m = 0, 1, 2, 3
n = 0, 1, 2, 3
o = 0, 1, 2 3,
R, R, R$_2$, R$_3$ = H, Alkyl Similarly analogs of other commercially useful MC-1 inhibitors are useful in this invention, such as analogs of fenpyroximate, as shown below. The parent structure of these compounds are commercially used as insecticides, but analogs of them may be radiolabeled for use as myocardial perfusion imaging agents.

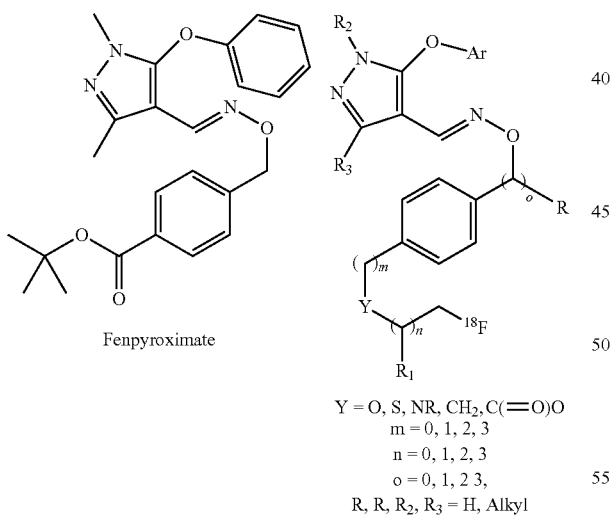

Fenpyroximate

Y = O, S, NR, CH$_2$, C(=O)O
m = 0, 1, 2, 3
n = 0, 1, 2, 3
o = 0, 1, 2 3,
R, R, R$_2$, R$_3$ = H, Alkyl Furthermore, analogs of the natural product piericidins, as shown below are useful as compounds as part of the invention. Piericidins are a class of compounds with variability in the substation and side chain, but can generally be characterized as a 2-alkyl-4-hydroxypyridine. Typically, in piericidins the 3, 5, and 6 positions also are substituted with either alkyl or alkoxy functionalities. Derivatives of these compounds and analogs may be radiolabeled for use as myocardial perfusion imaging agents.

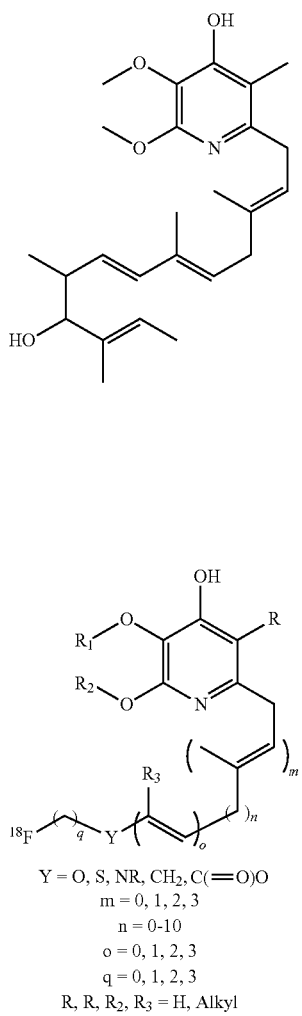

Y = O, S, NR, CH$_2$, C(=O)O
m = 0, 1, 2, 3
n = 0-10
o = 0, 1, 2, 3
q = 0, 1, 2, 3
R, R, R$_2$, R$_3$ = H, Alkyl Another class of compounds suitable for use in the invention is based on the commercial compound pyridaben. In some cases, the compound comprises a pyridazinone heterocycle attached via a lipophilic side chain to a radio-isotope, such as $^{18}$F-fluoride. These compounds may comprise a potent series of mitochondrial complex 1 inhibitors. The potency is retained throughout substitution of the groups X and Y for chalcogens, and the tolerance of the side chain (groups m, n, and Y) is wide, with branched and straight-chain groups of up to ten chain atoms still affording potent activity. In some embodiments, the compound is 2-alkyl-4-chloro-5-[4-(2-[$^{18}$F]fluoro-ethoxymethyl)-benzyloxy]-2H-pyridazin-3-one. For example, the compound may be 2-tert-butyl-4-chloro-5-[4-(2-[$^{18}$F]fluoro-ethoxymethyl)-benzyloxy]-2H-pyridazin-3-one.

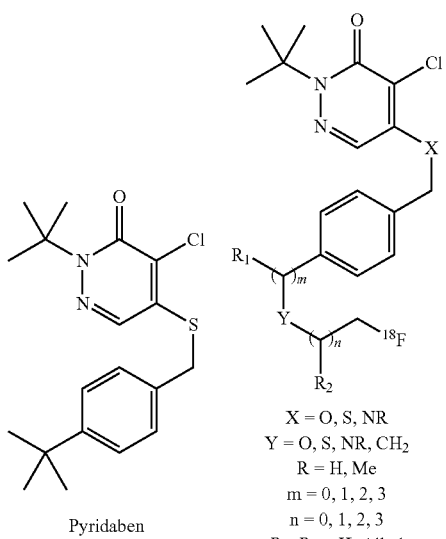

Pyridaben

X = O, S, NR
Y = O, S, NR, CH₂
R = H, Me
m = 0, 1, 2, 3
n = 0, 1, 2, 3
R₁, R₂ = H, Alkyl

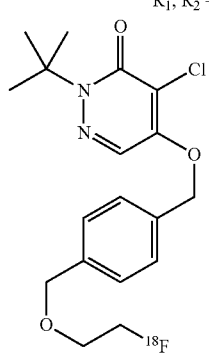

2-tert-Butyl-4-chloro-5-[4-(2-[¹⁸F]fluoro-ethoxymethyl)-benzyloxy]-2H-pyridazin-3-one or BMS-747158-02.

X = O, S, NR
Y = O, S, NR, CH₂
R = H, Me
m = 0, 1, 2, 3
n = 0, 1, 2, 3
R₁, R₂ = H, Alkyl The compounds described herein may be prepared by methods known to those skilled in the art of organic radiochemistry and those familiar with the techniques used for the manufacture of such radiopharmaceuticals as fluorodeoxyglucose (¹⁸F-FDG), for example, the only currently approved 18-F radiotracer for human imaging. The compounds may be purified prior to use and such methods are exemplified within this application. Other methods are readily available to the skilled artisan.

In some cases, the radiopharmaceutical compounds may include an asymmetric center, i.e., an asymmetrically substituted atom. Compounds containing an asymmetrically substituted atom may be isolated in optically active or racemic forms. It is well known in the art how to prepare optically active forms, including methods such as resolution of racemic forms or synthesis from optically active starting materials. Many geometric isomers of olefins, C=N double bonds, and the like can also be present in the compounds described herein, and all such stable isomers are contemplated for use in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be useful in the present invention.

As noted, the radiopharmaceutical compounds herein described may contain alkyl substituents. As that term may be used herein, "alkyl" and "alk" as may be employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or CF₃, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

As heretofore noted, the radiopharmaceutical compounds used herein also include "analogs" thereof. The term "analog" is meant to include any compounds that are substantially similar in structure or atom connectivity to the referred structure or compound. These include compounds in which one or more individual atoms have been replaced, either with a different atom, or with a different functional group. The term analog implies a high degree of homology, but also may include compounds that are intellectually derived from such a structure. Thus, by way of illustration, an analog of pyridaben may be taken as any compound containing a 2-alkyl-4-chloro-2H-pyridazin-3-one with a lipophilic side chain substituted at the 5-position.

The radiopharmaceutical compounds as part of the present invention are intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The radiopharmaceutical compounds hereinabove described are considered pharmaceutically acceptable. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The radiopharmaceutical compounds hereinabove described also include pharmaceutically acceptable salts. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts useful in the present invention can be synthesized from the parent radiopharmaceutical which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

As heretofore set forth, the radiopharmaceutical compounds herein utilized are preferably MC-1 inhibitors. The term "MC-1 inhibitor" refers to specific known compounds, and analogs of those compounds which have the ability to inhibit MC-1. Specifically compounds which may be radiolabeled with a suitable radioisotope such that an image of myocardial tissue may be obtained by administration of said compound to a patient, followed by scan the patient in a suitable camera, be it PET, SPECT or planar capable. Such inhibitors may include, but are not limited to, pyridaben and its analogs, fenazaquin and its analogs, rotenone and its analogs, deguelin and its analogs, and substituted chromone derivatives and their analogs, including those illustrated above.

The radiopharmaceutical compounds of the invention are preferably labeled with a suitable radioisotope. The term "suitable radioisotope" refers to isotopes that may be covalently incorporated into a molecule without detrimentally effecting the biological potency, and possessing decay parameters, such as sufficiently long half life, and suitable particle/emission energy such that a satisfactory image may be obtained. Such radioisotopes may include, but are not limited to, $^{11}C$, $^{13}N$, $^{18}F$, $^{86}Br$, $^{124}I$, $^{125}I$, and $^{131}I$. Of these, $^{18}F$ is particularly preferred for use with the invention.

Radiolabeling is accomplished using materials and techniques available to those skilled in the art. For example, radiolabeling with fluorine may be accomplished by electrophilic fluorination, using [$^{18}F$—F]fluorine gas under appropriate conditions, but is most preferably accomplished via nucleophilic displacement of an appropriate leaving group by [$^{18}F$]fluoride ion. The [$^{18}F$]-fluoride ion is rendered more reactive by the addition of kryptates to sequester the potassium counterion. The preferred leaving groups may be selected from those known to practitioners ordinarily skilled in the art, but are preferably halogens, including iodide, bromide, chloride and fluoride. Most preferably the leaving group is a alkyl or aryl sulfonated ester, specifically a toluenesulfonate ester.

In one set of embodiments, the radiopharmaceutical composition comprises 2-tert-butyl-4-chloro-5-[4-(2-[$^{18}F$]fluoro-ethoxymethyl)-benzyloxy]-2H-pyridazin-3-one, together with a stabilizer comprising ascorbic acid, wherein the pH of the composition is within the range of about 4-4.5 and the radiopharmaceutical composition comprises greater than about 50 mg of ascorbic acid per milliliter.

The stabilized radiopharmaceutical formulations of the invention may be prepared by addition of a first solution (e.g., an aqueous solution or ethanolic solution) comprising a crude (e.g., unpurified) or purified radiopharmaceutical compound to a second, prepared solution comprising ascorbic acid, to form a third solution comprising the radiopharmaceutical compound and ascorbic acid. The first solution may be an aqueous solution or an alcohol solution, such as an ethanolic solution. In some cases, the second solution is adjusted to the desired pH (e.g., pH in the range of 3.5-5.5) by addition of either an acidic solution (e.g., hydrochloric acid solution) or a basic solution (e.g., an aqueous solution of sodium hydroxide), prior to contact with the first solution.

Methods of the invention may include additional processing steps. For example, after addition of the first solution to the second solution, the third solution may be adjusted to a different pH, such as a pH within biological range, i.e., about 6-8. In some embodiments, the radiopharmaceutical composition comprises greater than about 50 mg of ascorbic acid per milliliter, and the method further comprises the step of adjusting the pH of the third solution to about less than 6, after addition of the first solution to the second solution.

In one set of embodiments, the method involves the addition of a first solution comprising 2-tert-butyl-4-chloro-5-[4-(2-[$^{18}F$]fluoro-ethoxymethyl)-benzyloxy]-2H-pyridazin-3-one, or a $^{19}F$ analog thereof, to a second solution comprising ascorbic acid, wherein the second solution has a pH within the range of about 4-4.5 and comprises greater than about 50 mg of ascorbic acid per milliliter, to form a third solution comprising the 2-tert-butyl-4-chloro-5-[4-(2-[$^{18}F$]fluoro-ethoxymethyl)-benzyloxy]-2H-pyridazin-3-one and ascorbic acid.

In some embodiments, the method may include one or more purification steps, such as purification by chromatography. For example, the method can include purification of the radiopharmaceutical compound via chromatography, i.e., prior to addition to a solution comprising ascorbic acid. The chromatography can be reverse-phase chromatography, regular-phase chromatography, and/or ion exchange chromatography. In some embodiments, the regular-phase chromatography may involve use of an alumina or silica gel column. In some cases, methods of the invention may involve use of a reverse phase HPLC column. For reverse phase chromatography, the HPLC column may be eluted using a mobile phase comprising water, acetonitrile, a buffer (e.g., ammonium acetate buffer), an alcohol (e.g., methanol, ethanol) an acid (e.g., formic acid), or mixtures thereof. In some cases, the HPLC column is a reverse phase column and the column is eluted using a mobile phase comprising ammonium acetate buffer, acetonitrile, ethanol, formic acid, or mixtures thereof.

The typical radiopharmaceutical composition of the invention comprises an aqueous solution containing not more than about 0-10% ethanol by volume, and greater than about 5 mg of ascorbic acid per milliliter. In some cases, the aqueous solution contains greater than about 10 mg, greater than about 20 mg, greater than about 30 mg, greater than about 40 mg, greater than about 50 mg, greater than about 100 mg, or, in some cases, greater than about 200 mg of ascorbic acid per milliliter of dosage form. In some embodiments, the aqueous solution also includes not more than about 20 mCi of a radiopharmaceutical compound (e.g., about 10-20 mCi) and not more than about 5 µg of the cold, $^{19}$F-analog of the radiotracer (e.g., about 1-5 µg) per each milliliter of dosage form. Radiolysis is typically initiated by the addition of Na$^{18}$F into the solution.

Some aspects of the invention relate to the discovery that, during development of radiopharmaceutical compositions according to the invention for widespread manufacture, distribution and use, ascorbic acid exhibits an enhanced ability to stabilize radiopharmaceutical preparations at certain pH values. It was found that at the pH values set forth herein, the radiopharmaceutical preparations exhibited significantly higher stability against decomposition. At higher pH values, the stabilization of these solutions was markedly less effective. Comparison of the pH of the ascorbic acid-containing solutions, the stability over a six hour period, and the pKa of ascorbic acid revealed that the most efficacious stabilization was in the range in which the oxidative center on the stabilizer was protonated.

In some cases, the use of ascorbic acid or its analogs in radiopharmaceutical compositions described herein can stabilize a radiopharmaceutical such that high radiochemical purity (e.g., >90%, >95%, >97%) can be maintained during the essentially the total lifetime of the radiopharmaceutical. For example, a radiopharmaceutical including $^{18}$F can be maintained at high radiochemical purity for 1 hour or greater, 2 hours or greater, or, in some cases, 5 hours or greater.

The invention also includes methods for administering a radiopharmaceutical composition to a subject. In some cases, the radiopharmaceutical composition contains ascorbic acid and has a pH within the range of about 3.5-5.5. In some cases, radiopharmaceutical composition contains ascorbic acid in an amount greater than about 50 mg of ascorbic acid per milliliter and has a pH that is less than about 6. In one set of embodiments, the invention provides a method for administering to a patient a radiopharmaceutical composition comprising 2-tert-butyl-4-chloro-5-[4-(2-[$^{18}$F]fluoro-ethoxymethyl)-benzyloxy]-2H-pyridazin-3-one, ascorbic acid in an amount greater than about 50 mg of ascorbic acid per milliliter, wherein the radiopharmaceutical composition has a pH that is less than about 6.

The compositions of the invention herein described may be administered in the following manner, by way of illustration: A catheter or heparin lock line is prepared into the vein of a subject, and is flush with the appropriate saline and or heparin solution. The dose is administered via luer-lock into the catheter or heparin lock line. The patient is either in situ in a PET camera, and imaging may commence immediately, or the patient is allowed to rest for a time prior to being placed in a PET camera. Alternatively, the patient, is dosed in a similar manner, via a catheter or heparin lock, under treadmill or pharmacological stress, using protocols similar to those known in the art.

The following examples utilize various embodiments of the invention, but should not be construed as limiting the scope thereof:

EXAMPLES

The integrity of a radiopharmaceutical is measured by the radiochemical purity (RCP) of the radiolabeled compound using ITLC or more preferably HPLC. The advantage of using HPLC is that radio-impurities caused by radiolytic degradation can be separated from the radiopharmaceutical under certain chromatographic conditions. Improved stability over time for radiopharmaceutical compositions of this invention can be demonstrated by determining the change in RCP of the radiolabeled compound in samples taken at representative time points. The radiopharmaceutical compositions of this invention are effective in maintaining the stability of samples for up to ten hours.

The initial RCP of a radiopharmaceutical is largely dependent on radiolabeling conditions such as pH, heating temperature and time. Once a radiopharmaceutical is prepared in high yield, the stability of the radiopharmaceutical composition is measured by the RCP change of the radiopharmaceutical over a certain period of time.

Acetic acid (ultra-pure), ammonium hydroxide (ultra-pure), and gentisic acid were purchased from either Aldrich or Sigma Chemical Co., and were used as received. Hydrochloric acid purchased from Fisher and sodium hydroxide (1 N solution) from VWR were used for pH adjustment. Ascorbic acid (500 mg/mL, USP injectable solution) was purchased from Myoderm Medical and diluted with sterile water for injection (SWFI) as required. Sodium [F-18] fluoride (Na$^{18}$F) was purchased from Siemens Biomarker Solutions as a salt deposited on a polymeric column support. The fluoride was eluted from the column into a reaction flask or vial using a solution of potassium carbonate ($K_2CO_3$) and Kryptofix [222].

The following HPLC analytical methods may be used. HPLC method 1 used a HP-1100 HPLC system with a UV/visible detector ($\lambda$=220 nm), an IN-US radio-detector, and a Zorbax $C_{18}$ column (4.6 mm×250 mm, 80 Å pore size). The flow rate was 1 mL/min with the mobile phase starting with 92% solvent A (0.025 M ammonium acetate buffer, pH 6.8) and 8% solvent B (acetonitrile) to 90% solvent A and 8% solvent B at 18 min, followed by an isocratic wash using 40% of solvent A and 60% solvent B from 19 to 25 min.

HPLC method 2 used a HP-1100 HPLC system with a UV/visible detector ($\lambda$=220 nm), an IN-US radio-detector, and a Zorbax $C_{18}$ column (4.6 mm×250 mm, 80 Å pore size). The flow rate was 1 mL/min with the mobile phase starting with 92% solvent A (0.025 M ammonium acetate buffer, pH 6.8) and 8% solvent B (acetonitrile) to 80% solvent A and 20% solvent B at 18 min, followed by an isocratic wash using 40% of solvent A and 60% solvent B from 19 to 25 min.

HPLC method 3 used a HP-1100 HPLC system with a UV/visible detector ($\lambda$=220 nm), an IN-US radio-detector, and a Zorbax $C_{18}$ column (4.6 mm×250 mm, 80 Å pore size). The flow rate was 1 mL/min with an isocratic mobile phase with 92% solvent A (0.025 M ammonium acetate buffer, pH 6.8) and 8% solvent B (acetonitrile) over 25 min, followed by an isocratic wash using 40% of solvent A and 60% solvent B from 26 to 30 min.

HPLC method 4 used a HP-1100 HPLC system with an EG&G Berthold Radioflow detector, and a Zorbax $C_{18}$ column (4.6 mm×50 mm, 1.8 µm particle size). The flow rate was 1 mL/min with the mobile phase of 50% acetonitrile/ 50% water in 0.1% formic acid with a run time of 12 min.

The following examples describe the preparation and purification of $^{18}$F-labeled myocardial perfusion imaging radiotracers. Using the following general procedure pyridaben, fenazaquin and chromone analogs were prepared in good yields, and formulated into stable radiopharmaceutical compositions.

Example 1

Synthetic Procedure for Preparation of $^{18}$F Myocardial Perfusion Imaging Radiotracer for pH Stabilization Studies Potassium carbonate ($K_2CO_3$, USP grade, 10 mg) was dissolved in distilled/deionized water ($H_2O$, 1 mL) and was added with agitation to a solution of 4,7,13,16,21,24-Hexaoxa-1,10-diazabicyclo[8.8.8]hexacosane (referred to as Kryptofix™, K222) in anhydrous acetonitrile ($CH_3CN$, 4 mL), and an aliquot of the resulting solution (1 mL) was used to elute the $^{18}$F-bearing resin column. The radioactivity content of the column eluate was determined and the elute was transferred to the reaction vessel of the Explora RN Chemistry Module. This system was controlled by computer using the GINA-Star software. The eluted complex solution was concentrated to dryness (70-95° C.), argon bleed; partial vacuum (250-12 mbar)). This afforded a relatively dry, highly activated form of [$^{18}$F]fluoride. The solution of the corresponding toluenesulfonate ester of the desired radiotracer dissolved in 100% acetonitrile was then added to the reaction vessel. The mixture was heated at 90° C. for 10 minutes.

Example 2

Purification of $^{18}$F Myocardial Perfusion Imaging Radiotracers and Preparation of Dose for pH Stabilization Studies After the reaction was complete, the acetonitrile was evaporated (55° C., argon bleed; partial vacuum (250-15 mbar)) and the reaction mixture was suspended in mobile phase (60% acetonitrile/40% 50 mM ammonium acetate in water, 1.3 mL). The mixture was drawn into a sample loop and injected onto a HPLC column (Phenomenex Synergi 4 µHydro-RP C18, 250×10 mm). The mixture was purified via chromatography under isocratic conditions (60% acetonitrile/40% 50 mM ammonium acetate in water, 5 ml/min, 36 min. run time). The radiosynthesis module (Explora RN Chemistry Module) is equipped with both UV (254 nm) and Geiger-Mueller (GM) detectors.

The fraction containing the labeled radio-tracer was collected into a vial. Ascorbic acid solution having an ascorbic acid concentration of 50 mg/mL (10-15 mL) was added, and the solution was passed through a Sep-Pak® cartridge (previously conditioned with 10 mL of ethanol followed by 10 mL of the ascorbic acid solution). The $^{18}$F radiolabeled tracer adsorbs onto the column and the aqueous eluate is discarded. The Sep-Pak® was washed with an additional aliquot of ascorbic acid solution (10 mL) to remove any additional by products and residual acetonitrile. The radiotracer was then eluted with ethanol (<0.5 mL) and added to a vial containing 9.5 mL of ascorbic acid solution.

Example 3

Determination of the Effect of pH Value on the Stabilization of Radiotracer Dose Solutions A series of ascorbic acid solutions at various pH values was formulated, each solution containing 5 µg/mL of a cold, $^{19}$F-analog of the radiopharmaceutical compound, 2-tert-butyl-4-chloro-5-[4-(2-[18F]fluoro-ethoxymethyl)-benzyloxy]-2H-pyridazin-3-one (e.g., BMS-747158-01 (API)), ethanol/water (5/95), and 50 mg/mL ascorbic acid. The pH of each solution was adjusted by addition of a stock aqueous solution of either hydrochloric acid or sodium hydroxide. as required. The list of solutions is shown in Table 1. Radiolysis was initiated by the addition of Na$^{18}$F into the solution containing the cold, $^{19}$F-analog of the radiopharmaceutical compound, and the solutions were monitored via the HPLC analysis method for radiochemical purity over a (minimum) 6 hour period. The solutions were analyzed using a C18 RP-HPLC column with a gradient mobile phase and the elution profile was monitored using both UV and radiochemical detectors. The results are shown in FIG. 1.

TABLE 1

Ascorbic acid solutions used in Example 3.

| Solution | Lot # | pH |
|---|---|---|
| A | 070327 | 4.0 |
| B | 070328 | 5.8 |
| C | 070330 | 4.0 |
| D | 070403 | 4.0 |
| E | 070404 | 4.5 |
| F | 070418 | 4.6 |
| G | 070424 | 4.6 |
| H | 070425 | 4.6 |
| I | 070501 | 6.5 |
| J | 070502 | 2.4 |

As can be seen from the graph in FIG. 1, the purity of the resultant solutions upon storage was directly dependent upon the pH of the initial buffered dosage. Solutions at higher pH values (closer to physiological pH of 7-7.5) had markedly less stability to storage than did those with relatively more acidic values. This is illustrated by the plots specifically with the solution pH values at 5.8 (Solution B) and 6.5 (Solution I), respectively. These are the two lowest plots on the graph shown in FIG. 1, respectively.

Figure 2:
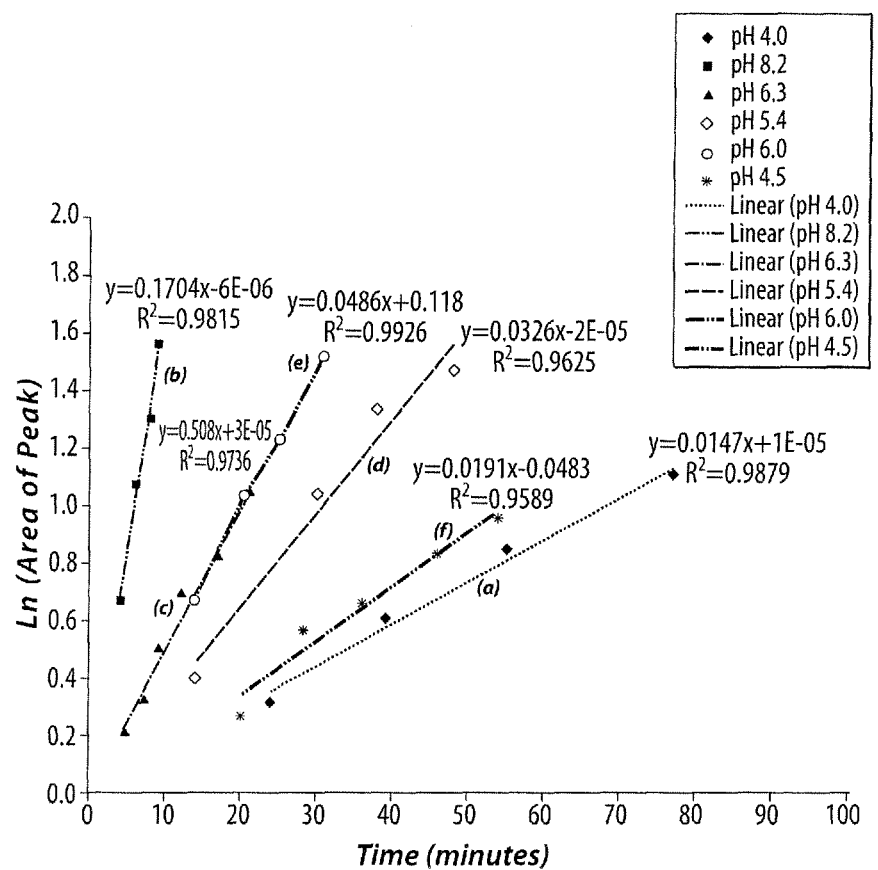
FIG. 2 shows a plot of the rate of radiochemical impurity formation for various compositions of the invention at a pH of (a) 4.0, (b) 8.2, (c) 6.3, (d), 5.4, (e) 6.0, and (f) 4.5.

Additional studies monitoring the formation of a radiochemical impurity as a function of solution pH over a range of 4.0 to 8.2, as shown in FIG. 2. For each solution the formation of radiochemical purity was monitored by HPLC, and the area of the chromatographic peak corresponding to the radiochemical impurities was plotted as a function of time. Solutions having a pH range between 3.5.-5.5 exhibited greater stability relative to solutions having a pH of 6.0 or greater, demonstrating a much slower rate of formation of radiochemical impurity. The results shown in FIG. 2 further demonstrate the effect of improved formulation stability under critical acidic conditions. Over the tested pH range the observed 1$^{st}$ order reaction rates for the formation of the radiochemical impurity is reduced by greater than a factor of 10.

Example 4

Figure 3:
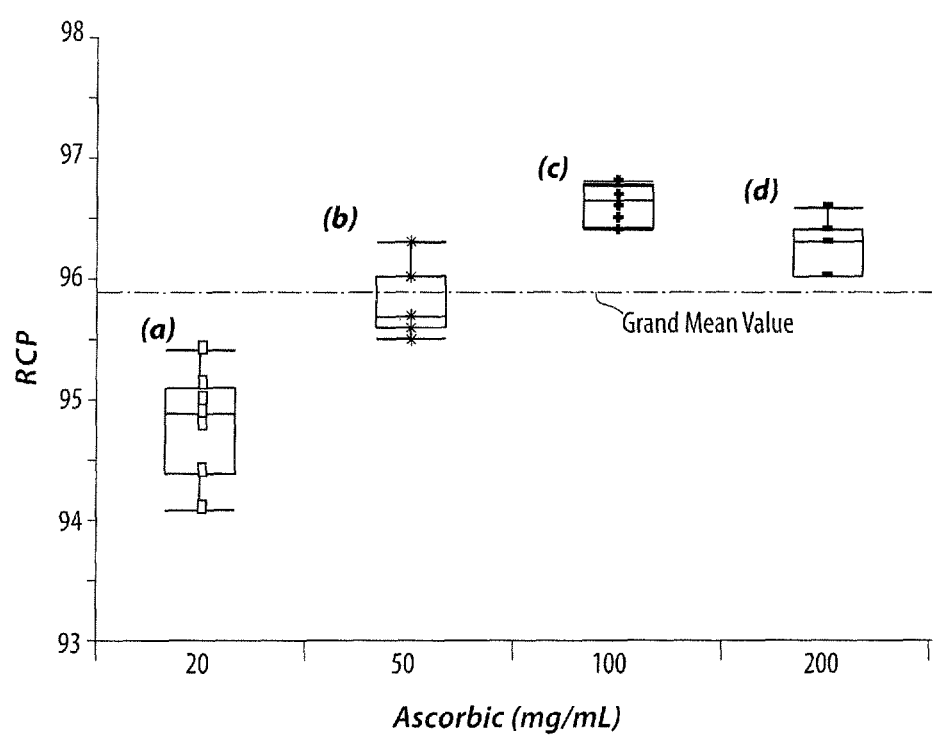
FIG. 3 shows a plot of radiochemical purity of a series of solutions comprising ascorbic acid at a concentration of (a) 20 mg/mL (|p|>0.001), (b) 50 mg/mL, (c) 100 mg/mL, (d) and 200 mg/mL.

Determination of the Effect of Ascorbic Acid Concentration on the Stabilization of Radiotracer Dose Solutions This example describes the effect of ascorbic acid concentration on radiochemical purity. In this example, the radiochemical purity (RCP) of the $^{18}$F-labeled drug product (2-tert-butyl-4-chloro-5-[4-(2-[$^{18}$F]fluoro-ethoxymethyl)-benzyloxy]-2H-pyridazin-3-one) was monitored for solutions having an ascorbic acid concentration range from 200 mg/mL (saturation level) to 20 mg/mL, at pH 5.8. The results shown in FIG. 3 indicate that the RCP levels do not significantly change over the 200 to 50 mg/mL range, but an increase in impurities (i.e., lower RCP level) was observed in the 20 mg/mL sample.

These examples are intended to illustrate the application of the invention and are in no way limiting in the intent, application and utility of the invention as set forth in the following claims.

What is claimed is:

1. A composition, comprising a radiopharmaceutical compound of formula:

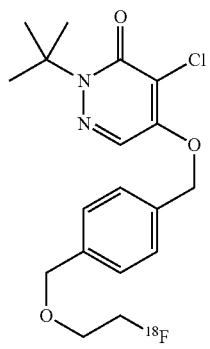 [SMILES: CC(C)(C)n1ncc(OCc2ccc(COCC[18F])cc2)c(Cl)c1=O]

and ascorbic acid,
wherein the pH of said composition is within a range of about 3.5 to less than 6; and
wherein the composition comprises between about 25 mg/mL and 500 mg/mL of ascorbic acid.

2. The composition of claim 1 wherein the composition comprises greater than about 50 mg/mL of ascorbic acid.

3. A method for preparing a radiopharmaceutical composition of claim 1, comprising:
contacting a first solution comprising a radiopharmaceutical compound of formula:

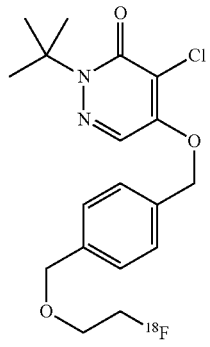 [SMILES: CC(C)(C)n1ncc(OCc2ccc(COCC[18F])cc2)c(Cl)c1=O]

with a second solution comprising ascorbic acid within a pH range of about 3.5 to less than 6, to form the radiopharmaceutical composition comprising the radiopharmaceutical compound and ascorbic acid,
wherein the composition comprises between about 25 mg/mL and 500 mg/mL of ascorbic acid.

4. A method of myocardial imaging a patient, comprising:
administering to the patient a radiopharmaceutical composition comprising a radiopharmaceutical compound of formula:

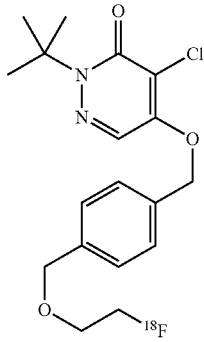 [SMILES: CC(C)(C)n1ncc(OCc2ccc(COCC[18F])cc2)c(Cl)c1=O]

and ascorbic acid,
wherein the pH of the composition is within a range of about 3.5 to less than 6, and
wherein the composition comprises between about 25 mg/mL and 500 mg/mL of ascorbic acid; and
obtaining a myocardial image of the patient.

5. The composition of claim 1, wherein the composition comprises between about 25 mg/mL and 200 mg/mL of ascorbic acid.

6. The composition of claim 1, wherein the composition comprises greater than about 40 mg/mL of ascorbic acid.

7. The composition of claim 1, wherein the composition comprises between about 50 mg/mL and 200 mg/mL of ascorbic acid.

8. The composition of claim 1, wherein the composition comprises about 50 mg/mL of ascorbic acid.

9. The composition of claim 1, wherein said pH is within the range of about 5.5 to less than 6.

10. The composition of claim 9, wherein the pH is 5.8.

11. The composition of claim 5, wherein said pH is within the range of about 5.5 to less than 6.

12. The composition of claim 11, wherein the pH is 5.8.

* * * * *